(12) United States Patent
Ward et al.

(10) Patent No.: US 7,837,040 B2
(45) Date of Patent: Nov. 23, 2010

(54) ACOUSTIC CONCENTRATION OF PARTICLES IN FLUID FLOW

(75) Inventors: Michael D. Ward, Los Alamos, NM (US); Gregory Kaduchak, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 11/784,936

(22) Filed: Apr. 9, 2007

(65) Prior Publication Data
US 2008/0245745 A1    Oct. 9, 2008

(51) Int. Cl.
*B03B 5/00*    (2006.01)

(52) U.S. Cl. .................. 209/210; 209/18; 209/156; 209/590

(58) Field of Classification Search ............ 209/18, 209/210, 156, 590; 210/748
See application file for complete search history.

(56) References Cited

U.S. PATENT DOCUMENTS

| | | | |
|---|---|---|---|
| 3,882,732 A | 5/1975 | Fletcher et al. | |
| 4,055,491 A | 10/1977 | Porath-Furedi | |
| 4,265,124 A | 5/1981 | Lim et al. | |
| 4,285,810 A | 8/1981 | Kirkland et al. | |
| 4,523,682 A * | 6/1985 | Barmatz et al. ............ 209/638 |
| 4,523,982 A | 6/1985 | Lee | |
| 4,604,542 A | 8/1986 | Thompson | |
| 4,673,512 A | 6/1987 | Schram | |
| 4,743,361 A | 5/1988 | Schram | |
| 4,743,631 A | 5/1988 | Greco et al. | |
| 4,759,775 A * | 7/1988 | Peterson et al. ............. 210/708 |
| 4,777,823 A | 10/1988 | Barmatz et al. | |
| 4,877,516 A | 10/1989 | Schram | |
| 4,964,303 A | 10/1990 | Barmatz et al. | |
| 4,979,824 A | 12/1990 | Mathies et al. | |
| 5,030,002 A | 7/1991 | North, Jr. | |
| 5,040,890 A | 8/1991 | North, Jr. | |
| 5,079,959 A | 1/1992 | Miyake et al. | |
| 5,085,783 A | 2/1992 | Feke et al. | |

(Continued)

FOREIGN PATENT DOCUMENTS

DE    3027433 A1    2/1982

(Continued)

OTHER PUBLICATIONS

Barmatz, M. et al., "Acoustic radiation potential on a sphere in plane, cylindrical, and spherical standing wave fields", *J. Acoust. Soc. Am.* 77 1985, 928-945.

(Continued)

*Primary Examiner*—Stefanos Karmis
*Assistant Examiner*—Kalyanavenkateshware Kumar
(74) *Attorney, Agent, or Firm*—Woodcock Washburn, LLP

(57) ABSTRACT

An apparatus for acoustic concentration of particles in a fluid flow includes a substantially acoustically transparent membrane and a vibration generator that define a fluid flow path therebetween. The fluid flow path is in fluid communication with a fluid source and a fluid outlet and the vibration generator is disposed adjacent the fluid flow path and is capable of producing an acoustic field in the fluid flow path. The acoustic field produces at least one pressure minima in the fluid flow path at a predetermined location within the fluid flow path and forces predetermined particles in the fluid flow path to the at least one pressure minima.

31 Claims, 4 Drawing Sheets

U.S. PATENT DOCUMENTS

| | | | |
|---|---|---|---|
| 5,164,094 A | | 11/1992 | Stuckart |
| 5,225,089 A * | | 7/1993 | Benes et al. ............... 210/748 |
| 5,376,551 A | | 12/1994 | Yoshikami |
| 5,395,588 A | | 3/1995 | North, Jr. et al. |
| 5,504,337 A | | 4/1996 | Lakowicz et al. |
| 5,527,460 A | | 6/1996 | Trampler et al. |
| 5,528,045 A | | 6/1996 | Hoffman et al. |
| 5,547,849 A | | 8/1996 | Baer et al. |
| 5,626,767 A * | | 5/1997 | Trampler et al. ............ 210/748 |
| 5,644,388 A | | 7/1997 | Maekawa et al. |
| 5,674,698 A | | 10/1997 | Zarling et al. |
| 5,711,888 A | | 1/1998 | Trampler et al. |
| 5,739,902 A | | 4/1998 | Gjelsnes et al. |
| 5,798,222 A | | 8/1998 | Goix |
| 5,800,861 A | | 9/1998 | Chiang et al. |
| 5,831,166 A | | 11/1998 | Kozuka et al. |
| 5,981,180 A | | 11/1999 | Chandler et al. |
| 6,003,388 A | | 12/1999 | Oeftering |
| 6,055,859 A * | | 5/2000 | Kozuka et al. ................ 73/570 |
| 6,090,295 A | | 7/2000 | Raghavarao et al. |
| 6,216,538 B1 * | | 4/2001 | Yasuda et al. ............. 73/570.5 |
| 6,221,258 B1 | | 4/2001 | Feke et al. |
| 6,248,590 B1 | | 6/2001 | Malachowski |
| 6,255,118 B1 | | 7/2001 | Alfano et al. |
| 6,309,886 B1 | | 10/2001 | Ambrose et al. |
| 6,332,541 B1 | | 12/2001 | Coakley et al. |
| 6,348,687 B1 | | 2/2002 | Brockmann et al. |
| 6,373,567 B1 | | 4/2002 | Wise et al. |
| 6,449,563 B1 | | 9/2002 | Dukhin et al. |
| 6,467,350 B1 | | 10/2002 | Kaduchak et al. |
| 6,592,821 B1 | | 7/2003 | Wada et al. |
| 6,644,118 B2 | | 11/2003 | Kaduchak et al. |
| 6,683,314 B2 | | 1/2004 | Oostman, Jr. et al. |
| 6,713,019 B2 | | 3/2004 | Ozasa et al. |
| 6,797,158 B2 | | 9/2004 | Feke et al. |
| 6,813,017 B1 | | 11/2004 | Hoffman et al. |
| 6,816,257 B2 | | 11/2004 | Goix |
| 6,831,279 B2 | | 12/2004 | Ho |
| 6,881,314 B1 | | 4/2005 | Wang et al. |
| 7,008,540 B1 * | | 3/2006 | Weavers et al. ............. 210/636 |
| 7,018,819 B2 | | 3/2006 | Orwar et al. |
| 7,081,192 B1 | | 7/2006 | Wang et al. |
| 7,108,137 B2 * | | 9/2006 | Lal et al. .................... 209/659 |
| 7,113,266 B1 | | 9/2006 | Wells |
| 7,161,665 B2 | | 1/2007 | Johnson |
| 7,315,357 B2 | | 1/2008 | Ortyn et al. |
| 7,362,432 B2 | | 4/2008 | Roth |
| 7,403,125 B2 | | 7/2008 | Rich |
| 7,477,363 B2 | | 1/2009 | Nagai |
| 7,570,676 B2 | | 8/2009 | Essaian et al. |
| 2002/0121285 A1 | | 9/2002 | Poniatowski et al. |
| 2002/0162393 A1 | | 11/2002 | Kaduchak et al. |
| 2004/0057866 A1 | | 3/2004 | Zumeris et al. |
| 2004/0139792 A1 | | 7/2004 | Cobb |
| 2005/0072677 A1 | | 4/2005 | Gascoyne et al. |
| 2006/0021437 A1 | | 2/2006 | Kaduchak et al. |
| 2006/0163166 A1 | | 7/2006 | Hawkes et al. |
| 2007/0071683 A1 | | 3/2007 | Dayton et al. |
| 2007/0098232 A1 | | 5/2007 | Matula et al. |
| 2008/0053787 A1 * | | 3/2008 | Bagajewicz ................. 196/111 |
| 2008/0106736 A1 | | 5/2008 | Graves et al. |
| 2008/0245709 A1 | | 10/2008 | Kaduchak et al. |
| 2009/0029870 A1 | | 1/2009 | Ward et al. |
| 2009/0042239 A1 | | 2/2009 | Ward et al. |
| 2009/0042310 A1 | | 2/2009 | Ward et al. |
| 2009/0045107 A1 | | 2/2009 | Ward et al. |
| 2009/0048805 A1 | | 2/2009 | Kaduchak et al. |
| 2009/0050573 A1 | | 2/2009 | Ward et al. |
| 2009/0053686 A1 | | 2/2009 | Ward et al. |
| 2009/0107241 A1 | | 4/2009 | Goddard et al. |
| 2009/0139332 A1 | | 6/2009 | Goddard et al. |
| 2009/0158823 A1 | | 6/2009 | Kaduchak et al. |
| 2009/0162887 A1 | | 6/2009 | Kaduchak et al. |
| 2009/0316151 A1 | | 12/2009 | Matula et al. |
| 2010/0000325 A1 | | 1/2010 | Kaduchak et al. |
| 2010/0009333 A1 | | 1/2010 | Auer |

FOREIGN PATENT DOCUMENTS

| | | |
|---|---|---|
| EP | 0 147 032 | 3/1985 |
| EP | 0 292 470 | 11/1988 |
| EP | 0 773 055 A2 | 5/1997 |
| FR | 821419 | 12/1937 |
| GB | 500271 | 12/1937 |
| JP | 63139231 A | 6/1988 |
| JP | 06241977 A | 9/1994 |
| JP | 08266891 A | 10/1996 |
| WO | WO 88/09210 | 12/1988 |
| WO | 90/05008 | 5/1990 |
| WO | WO 94/29695 | 12/1994 |
| WO | WO 97/02482 | 1/1997 |
| WO | WO 00/41794 | 7/2000 |
| WO | WO 02/072234 | 9/2002 |
| WO | WO 02/072236 | 9/2002 |
| WO | WO 03/079006 | 9/2003 |
| WO | WO 2004/024287 | 3/2004 |
| WO | WO 2004/033087 A1 | 4/2004 |
| WO | WO 2007/128795 | 11/2007 |
| WO | WO 2008/122051 | 10/2008 |
| WO | WO 2009/091925 | 7/2009 |

OTHER PUBLICATIONS

Bauerecker, Sigurd et al., "Formation and growth of ice particles in stationary ultrasonic fields", *J. of Chem. Phys.* 1998, 3709-3712.

Beverloo, H. B. et al., "Inorganic Phsophors as New Luminescent Labels for Immunocytochemistry and Time-Resolved Microscopy", *Cytometry 11* 1990, 784-792.

Bienvenue, Joan M. et al., "Microchip-Based Cell Lysis and DNA Extraction from Sperm Cells for Application to Forensic Analysis", *J. Forensic Sci. 51* 2006, 266-273.

Binks, Bernard P. et al., "Modern Aspects of Emulsion Science", *The Royal Society of Chemistry* 1998, 310-321.

Bishop, J. E. et al., "Mechanism of higher brightness of PerCP-Cy5.5", *Cytometry Supp* vol. 10 2000, 162-163.

Bossuyt, Xavier et al., "Comparative Analysis for Whole Blood Lysis Methods for Flow Cytometry", *Cytometry 30* 1997, 124-133.

Caperan, Ph. et al., "Acoustic Agglomeration of a Glycol Fog Aerosol: Influence of Particle Concentration and Intensity of the Sound Field at Two Frequencies", *J. Aerosol Sci. 26* 1995, 595-612.

Chase, Eric S. et al., "Resolution of Dimly Fluorescent Particles: A Practical Measure of Fluorescence Sensitivity", *Cytometry 33* 1998, 267-279.

Coakley, W. T. et al., "Analytical scale ultrasonic standing wave manipulation of cells and microparticles", *Ultrasonics 38* 2000, 638-641.

Condrau, Marc A. et al., "Time-Resolved Flow Cytometry for the Measurement of Lanthanide Chelate Fluorescence: I. Concept and Theoretical Evaluation", *Cytometry 16* 1994, 187-194.

Condrau, Marc A. et al., "Time-Resolved Flow Cytometry for the Measurement of Lanthanide Chelate Fluorescence: II. Instrument Design and Experimental Results", *Cytometry 16* 1994, 195-2005.

Dean, Phillip N. et al., "Hydrodynamic Orientation of Sperm Heads for Flow Cytometry", *Biophys. J. 23* 1978, 7-13.

Doblhoff-Dier, O. et al., "A Novel Ultrasonic Resonance Field Device for the Retention of Animal Cells", *Biotechnol. Prog. 10* 1994, 428-432.

Donnert, Gerald et al., "Major signal increase in fluorescence microscopy through dark-state relaxation", *Nature Methods 4* 2007, 81-86.

Doornbos, Richard M. et al., "Experimental and Model Investigations of Bleaching and Saturation of Fluorescence in Flow Cytometry", *Cytometry 29* 1997, 204-214.

Fenniri, Hicham et al., "Classification of Spectroscopically Encoded Resins by Raman Mapping and Infrared Hyperspectral Imaging", *Journal of Combinatorial Chemistry 8* 2006, 192-198.

Fulwyler, Mack J. et al., "Hydronamic Orientation of Cells", *Histochem. Cytoche. 7* 1977, 781-783.

Gaida, Th. et al., "Selective Retention of Viable Cells in Ultrasonic Resonance Field Devices", *Biotech. Prog. 12* 1996, 73-76.

Gallego Juarez, J. A. et al., "Piezoelectric Transducer for Air-Borne Ultrasound", *Acustica 29* 1973, 234-239.

Gao, Xiaohu et al., "Quantum Dot-Encoded Mesoporous Beads with High Brightness and Uniformity: Rapid Readout Using Flow Cytometry", *Anal. Chem. 76* 2004, 2406-2410.

Goddard, Gregory et al., "Single Particle High Resolution Spectral Analysis Flow Cytometry", *Cytometry 69A* 2006, 842-851.

Goddard, Gregory et al., "Ultrasonic particle concentration in a line-driven cylindrical tube", *J. Acoust. Soc. Am. 117* 2005, 3440-3447.

Goddard, Gregory et al., "Ultrasonic Particle-Concentration for Sheathless Focusing of Particles for Analysis in a Flow Cytometer", *Cytometry 69* 2006, 66-74.

Gor'kov, L. P. et al., "On the forces acting on a small particle in an acoustical field in an ideal fluid", *Soviet Physics-Doklady 6* 1962, 773-775.

Gould, R. K. et al., "The effects of acoustic forces on small particles in suspension", *in Proceedings of the 1973 Symposium on Finite Amplitude Wave Effects in Fluids, edited by L. Bjorno, Pergamon, Guilford* 1974, 252-257.

Gupta, Sanjay et al., "Acoustically driven collection of suspended particles within porous media", *Ultrasonics 35* 1997, 131-139.

Gupta, Sanjay et al., "Fractionation of Mixed Particulate Solids According to Compressibility Using Ultrasonic Standing Wave Fields", *Chem. Eng. Sci. 50* 1995, 3275-3284.

Haake, A. et al., "Positioning of small particles by an ultrasound field excited by surface waves", *Ultrasonics 42* 2004, 75-80.

Habbersett, Robert C. et al., "An Analytical System Based on a Compact Flow Cytometer for DNA Fragment Sizing and Single Molecule Detection", *Cytometry 60A* 2004, 125-134.

Harma, Harri et al., "Zeptomole detection sensitivity of prostate-specific antigen in a rapid microtitre plate assay using time-resolved fluorescence", *Luminescence 15* 2000, 351-355.

Harrison, Benjamin S. et al., "Near-Infrared Photo- and Electroluminescence of Alkoxy-Substituted Poly (p-phenylene) and Nonconjugated Polymer/Lanthanide Tetraphenylporphyrin Blends", *Chemistry of Materials 16* 2004, 2938-2947.

Hawkes, Jeremy J. et al., "A laminar flow expansion chamber facilitating downstream manipulation of particles concentrated using an ultrasonic standing wave", *Ultrasonics 36* 1998, 901-903.

Hawkes, Jeremy J. et al., "Ultrasonic deposition of cells on a surface", *Biosensors and Bioelectronics 19* 2004, 1021-1028.

Hemmila, I. et al., "Progress in Lanthanides as Luminescent Probes", *J. Fluoresnicence 15* 2005, 529-542.

Higashitani, Ko et al., "Migration of Suspended Particles in Plane Stationary Ultrasonic Field", *Chem. Eng. Sci. 36* 1981, 1187-1192.

Hirschfeld, Tomas et al., "Fluorescence Background Discrimination by Prebleaching", *J. Histochem. and Cytochem. 27* 1979, 96-101.

Holmes, David et al., "High throughput particle analysis: Combining dielectrophoretic particle focussing with confocal optical detection", *Biosensors and Bioelectronics 21* 2006, 1621-1630.

Huhtinen, Petri et al., "Synthesis, Characterization, and Application of Eu(III), Tb(III), Sm (III), and Dy(III) Lanthanide Chelate Nanoparticle Labels", *Anal. Chem. 77* 2005, 2643-2648.

Johnston, Paul A. et al., "Cellular platforms for HTS: three case studies", *DDT 7* 2002, 353-363.

Jonsson, Henrik et al., "Particle separation using ultrasound can be used with human shed mediastinal blodd", *Perfusion 20* 2005, 39-43.

Kaye, Paul H. et al., "Spatial light-scattering analysis as a means of characterizing and classifying non-spherical particles", *Meas. Sci. Technol. 9* 1998, 141-149.

King, Louis V. et al., "On the Acoustic Radiation Pressure on Spheres", *Proc. R. Soc. A. 147* 1933, 212-240.

Kogan, Shulim et al., "Acoustic concentration of particles in piezoelectric tubes: Theoretical modeling of the effect of cavity shape and symmetry breaking", *J. Acoust. Soc. Am. 116* 2004, 1967-1974.

Kumar, Manoj et al., "Fractionation of Cell Mixtures Using Acoustic and Laminar Flow Fields", *Biotech. Bioeng. 89* 2005, 129-137.

Kundt, A et al., "Longitudinal vibrations and acoustic figures in cylindrical columns of liquids", *Annalen der Physik And Chemie (Poggendorff's Annalen)* 153 1874, 1-12.

Leif, Robert C. et al., "Increasing the Luminescence of Lanthanide Complexes", *Cytometry 69A* 2006, 767-778.

Leif, R. C. et al., "Markers for Instrumental Evaluation of Cells of the Female Reproductive Tract; Existing and New Markers", *in The Automation of Uterine Cancer Cytology(edited by G. L. Wied, G. F. Babr, P.H. Bartels). Tutorials of Cytology* 1976, 313-344.

Lierke, E. G. et al., "Acoustic Positioning for Space Processing of Materials Science Samples in Mirror Furnaces", *IEEE Ultrasonics Symposium* 1983, 1129-1139.

Loken, Michael R. et al., "Cell Discrimination by Multiangle Light Scattering", *Histochem. Cytochem. 24* 1976, 284-291.

Loken, Michael R. et al., "Identification of Cell Asymmetry and Orientation by Light Scattering", *Histochem. Cytochem. 7* 1977, 790-795.

Macey, M. G. et al., "Comparative Study of Five Commercial Reagents for Preparing Normal and Leikaemic Lymphoctyes for Immunophenotypic Analysis by Flow Cytometry", *Cytometry 38* 1999, 153-160.

Maltsev, Valeri P. et al., "Scanning flow cytometry for individual particle analysis", *Review of Scientific Instruments 71* 2000, 243-255.

Martin, K. M. et al., "Acoustic filtration and sedimentation of soot particles", *Experiments in Fluids 23* 1997, 483-488.

Masudo, Takashi et al., "Particle Characterization and Separation by a Coupled Acoustic-Gravity Field"*Analytical Chemistry 73* 2001, 3467-3471.

Mathies, Richard A. et al., "Optimization of High-Sensitivity Fluorescence Detection", *Anal. Chem. 62* 1990, 1786-1791.

Meindersma, G. W. et al., "Separation of a biocatalyst with ultrafiltration or filtration after bioconversion", *J. Membrane Sci. 125* 1997, 333-349.

Mullaney, P. F. et al., "The Small Angle Light Scattering of Biological Cells", *Biophys. J. 10* 1970, 764-772.

Neukammer, Jorg et al., "Angular distribution of light scattered by single biological cells and oriented particle agglomerates", *Appl. Opt. 42* 2003, 6388-6397.

Nolan, John P. et al., "Suspension Array Technology: New Tools for Gene and Protein Analysis", *Cellular and Molecular Biology 47* 2001, 1241-1256.

Otaki, Masahiro et al., "Virus Removal in a Membrane Separation Process", *Water Sci. and Tech. 37* 1998, 107-116.

Petersson, Filip et al., "Carrier Medium Exchange through Ultrasonic Particle Switching in Microfluidic Channels", *Anal. Chem. 77* 2005, 1216-1221.

Petersson, Filip et al., "Free Flow Acoustophoresis: Microfluidic-Based Mode of Particle and Cell Separation", *Anal. Chem. 79* 2007, 5117-5123.

Pregibon, Daniel C. et al., "Multifunctional Encoded Particles for High-Throughput Biomolecule Analysis", *Science 315* 2007, 1393-1396.

Princen, Katrien et al., "Evaluation of SDF-1/CXCR4-Induced Ca2+ Signaling by Fluorometric Imaging Plate Reader (FLIPR) and Flow Cytometry", *Cytometry 51A* 2003, 35-45.

Rao, G. V. Rama et al., "Monodisperse Mesoporous Silica Microspheres Formed by Evaporation-Induced Self Assembly of Surfacant Templates in Aerosols", *Advanced Materials 18* 2002, 1301-1304.

Rens, Wim et al., "A Novel Nozzel for More Efficient Sperm Orientation to Improve Sorting Efficiency of X and Y Chromosome-Bearing Sperm", *Cytometry 33* 1998, 476-481.

Ricks, David C. et al., "A numerically stable global matrix method for cylindrically layered shells excited by ring forces", *J. Acoust. Soc. Am. 95* 1994, 3339-3349.

Rouleau, Francois et al., "Electromagnetic scattering by compact clusters of spheres", *Astron. Astrophvs. 310* 1996, 686-698.

Samiotaki, Martina et al., "Seven-Color Time-Resolved Fluorescence Hybridization Analysis of Human Papilloma Virus Types", *Analytical Biochemistry 253* 1997, 156-161.

Schoell, Wolfgang M. et al., "Separation of Sperm and Vaginal Cells with Flow Cytometry for DNA Typing After Sexual Assault", *Obstetrics and Gynecology 94* 1999, 623-627.

Semianov, K. A. et al., "Measurement of Mammalian Erythrocyte Indices from Light Scattering with Scaning Flow Cytometer", *Proc. SPIE 5141* 2003, 106-113.

Sethu, Palaniappan et al., "Continuous Flow Microfluidic Device for Rapid Erythrocyte Lysis", *Anal. Chem. 76* 2004, 6247-6253.

Shapiro, Howard M. et al., "Practical Flow Cytometry", *Hoboken, NJ, John Wiley & Sons, Inc.* 2005, 9-13.

Shvalov, Alexander N. et al., "Individual *Escherichia coli* Cells Studied from Light Scattering with the Scanning Flow Cytometer", *Cytometry 41* 2000, 41-45.

Shvalov, Alexander N. et al., "Light -scattering properties of individual erythrocytes", *Applied Optics 38* 1999, 230-235.

Slomkowski, Stanislaw et al., "New Typed of Microspheres and Microsphere-related Materials for Medical Diagnostics", *Polymers for Advanced Technologies 13* 2002, 906-918.

Steinkamp, J. A. et al., "Enhanced Immunofluorescence Measurement Resolution of Surface Antigens on Highly Autofluorescent, Glutaraldehyde-Fixed Cells Analyzed by Phase-Sensitive Flow Cytometry", *Cytometry 37* 1999, 275-283.

Stoffel, C. L. et al., "Data Analysis for a Dual Analysis for a Dual-Channel Virus Counter", *Analytical Chemistry* vol. 7, Dept. of Chemistry & Biochemistry, University of Colorado 2005.

Stoffel, C. L. et al., "Design and Characterization of a Compact Dual Channel Virus Counter", *Cytometry Part A 65A* Dept. of Chemistry and Biochemistry, University of Colorado 2005, 140-147.

Stovel, Richard T. et al., "A Means for Orienting Flat Cells in Flow Systems", *Biophys. J. 23* 1978, 1-5.

Thiessen, David B. et al., "Principles of some Acoustical, Electrical, and Optical Manipulation Methods with Applications to Drops, Bubbles, and Capillary Bridges", *ASME Fluids Eng. Div. Publ. FED* 1998.

Thiessen, David B. et al., "Some Responses of Small Diffusion Flames to Ultrasonic Radiation", *NASA* 2003, 321-324.

Trinh, E. H. et al., "Compact acoustic levitation device for studies in fluid dynamics and material science in the laboratory and microgravity", *Rev. Sci. Instrum. 56* 1985, 2059-2065.

Tung, Yi-Chung et al., "PDMS-based opto-fluidic micro flow cytometer with two-color, multi-angle fluorescence detection capability using PIN photodiodes", *Sensors and Actuators 98* 2004, 356-367.

Van Hee, P. et al., "Strategy for Selection of Methods for Separation of Bioparticles From Particle Mixtures", *Biotech. Bioeng. 94* 2006, 689-709.

Wang, Zhaowei et al., "Retention and Viability Characteristics of Mammalian Cells in an Acoustically Driven Polymer Mesh", *Biotechnol. Prog. 20* 2004, 384-387.

Ward, Michael et al., "Manipulation of Immunomagnetic Targets in Mircrofluidic Channel Flow", *Dissertation* 2005, 1-205.

Weiser, Mary Ann H. et al., "Extension of acoustic levitation to include the study of micron-size particles in a more compressible host liquid", *J. Acoust. Soc. Am. 71* 1982, 1261-1268.

Whitworth, Glenn et al., "Particle column formation in a stationary ultrasonic field", *J. Acoust. Soc. Am. 91* 1992, 79-85.

Whitworth, G. et al., "Transport and harvesting of suspended particles using modulated ultrasound", *Ultrasonics 29* 1991, 439-444.

Wu, Yang et al., "Diazo Coupling Method for Covalent Attachment of Proteins to Solid Substrates", *Bioconjugate Chem. 17* 2006, 359-365.

Yamakoshi, Yoshiki et al., "Micro particle trapping by opposite phases ultrasonic travelling waves", *Ultrasonics 36* 1998, 873-878.

Yasuda, Kenji et al., "Blood Concentration by Superposition of Higher Harmonics of Ultrasound", *Jpn. J. Appl. Phys. 36* 1997, 3130-3135.

Yasuda, Kenji et al., "Using acousitc radiation force as a concentration method for erythrocytes", *J. Acoust. Soc. Am 102* 1997, 642-645.

Ye, Chao-Hong et al., "Preparation of three terbium complexes with p-aminobenzoic acid and investigation of crystal structure influence on luminescence property", *Journal of Solid State Chemistry 177* 2004, 3735-3742.

Yurkin, Maxim A. et al., "Experimental and theoretical study of light scattering by individual mature red blook cells by use of scanning flow cytometry and a discrete dipole approximation", *Applied Optics 44* 2005, 5249-5256.

Aboobaker, N. et al., "Mathematical modeling of the movement of suspended particles subjected to acoustic and flow fields", *App. Math. Modeling 29* 2005, 515-532.

Anderson, M. et al., "The Physics and Technology of Ultrasonic Particle Separation in Air", *WCU* 2003, 1615-1621.

Apfel, R. E. et al., "Acoustic Radiation Pressure—Principles and Application to Separation Science", *Fortschritte Der Akustik DAGA '90* 1990, 19-30.

Araz, Muhammet K. et al., "Ultrasonic Separation in Microfluidic Capillaries", *IEEE Ultrasonics Symposium* 2003, 1066-1069.

Asai, K. et al., "Ultrasonic treatment of slurry", *Third International Coal Preparation Conference* 1958, 518-527.

Bazou, Despina et al., "Physical Environment of 2-D Animal Cell Aggregates Formed in a Short Pathlength Ultrasound Standing Wave Trap", *Ultrasound in Med. & Biol. 31* 2005, 423-430.

Benes, E. et al., "Abscheidung Dispergierter Teilchen Durch Ultraschall-Induzierte Koagulation", *Tagung der Deutschen Arbeitsgameinschaft fur Akustik-DAGA '89* 1989, 1-4.

Benes, E. et al., "Improved quartz crystal microbalance technique", *J. Appl. Phys. 56* 1984, 608-626.

Borthwick, K. A. et al., "Development of a novel compact sonicator for cell disruption", *J. of Microbiological Methods 60* 2005, 207-216.

Bosma, Rouke et al., "Ultrasound, a new separation technique to harvest microlalgae", *J. Appl. Phycology 15* 2003, 143-153.

Coakley, W. T. et al., "Cell-cell contact and membrane spreading in an ultrasound trap", *Colloids and Surfaces B: Biointerfaces 34* 2004, 221-230.

Coakley, W. T. et al., "Ultrasonic separations in analytical biotechnology", *Tibtech 15* 1997, 506-511.

Cousins, C. M. et al., "Plasma Preparation from Whole Blood Using Ultrasound", *Ultrasound in Med. & Biol. 26* 2000, 881-888.

Curtis, H. W. et al., "Ultrasonic Continuous Flow Plasmapheresis Separator", *IBM Tech. Disc. Bulletin 25* 1982, 192-193.

Czyz, Henryka et al., "On the Concentration of Aerosol Particles by Means of Drift Forces in a Standing Wave Field", *Acustica 70* 1990, 23-28.

Dain, Y. et al., "Dynamics of Suspended Particles in a Two-Dimensional High-Frequency Sonic Field", *J. Aerosol Sci. 26* 1995, 575-594.

Dain, Y. et al., "Side drift of aerosols in two-dimensional resonant acoustic levitators", *J. Acoust. Soc. Am 102* 1997, 2549-2555.

Danilov, S. D. et al., "Mean force on a small sphere in a sound field in a viscous fluid", *J. Acoust. Soc. Am. 107* 2000, 143-153.

Danilov, S. D. et al., "The Mean Force Acting on a Small Body in an Axisymmetric Sound Field in a Real Medium", *Izvestiya Adademii Nauk SSSR, Mekhanika Zhidkosti I Gaza 5* 1985, 812-820.

Doinikov, Alexander A. et al., "Acoustic radiation force on a spherical particle in a viscous heat-conducting fluid. I. General formula", *J. Acoust. Soc. Am. 101* 1997, 713-721.

Doinikov, Alexander A. et al., "Acoustic radiation force on a spherical particle in a viscous heat-conducting fluid. II. Force on a rigid sphere", *J. Acoust. Soc. Am. 101* 1997, 722-730.

Doinikov, Alexander A. et al., "Acoustic radiation force on a spherical particle in a viscous heat-conducting fluid. III. Force on a liquid drop", *J. Acoust. Soc. Am. 101* 1997, 731-740.

Doinikov, A. A. et al., "Acoustic radiation pressure on a rigid sphere in a viscous fluid", *Proc. R. Soc. Lond. 447* 1994, 447-466.

Gherardini, Lisa et al., "A New Immobilisation Method to Arrange Particles in a Gel Matrix by Ultrasound Standing Waves", *Ultrasound in Med. & Biol. 31* 2005, 261-272.

Goddard, Gregory R. et al., "Ultrasonic Concentration in a Line Driven Cylindrical Tube", *Dissertation* 2004, 1-276.

Gonzalez, Itziar et al., "Precise Measurements of Particle Entertainment in a Standing-Wave Acoustic Field Between 20 and 3500 Hz", *J. Aerosol Sci. 31* 2000, 1461-1468.

Gould, Robert K. et al., "Upper sound pressure limits on particle concentration in fields of ultrasonic standing-wave at megahertz frequencies", *Ultrasonics 30* 1992, 239-244.

Groschl, Martin et al., "Automatische Frequenzregelung fur Piezoelektrische Resonatoren und deren Implementierung in akustischen Driftwellenresonator", *Diplomarbeit Institut fur Allgemeine Physik, Technishchen Universitat Wien* 1991, 1-132.

Grossner, Michael T. et al., "Single fiber model of particle retention in an acoustically driven porous mesh", *Ultrasonics 41* 2003, 65-74.

Grossner, Michael T. et al., "Single-Collector Experiments and Modeling of Acoustically Aided Mesh Filtration", *Amer. Inst. Of Chem. Eng. 51* 2005, 1590-1598.

Grossner, Michael T. et al., "Transport analysis and model for the performace of an ultrasonically enhanced filtration process", *Chem. Eng. Sci. 60* 2005, 3233-3238.

Haake, Albrecht et al., "Contactless micromanipulation of small particles by an ultrasound field excited by a vibrating body", *J. Acoust. Soc. Am. 117* 2005, 2752-2760.

Haake, Albrecht et al., "Manipulation of Cells Using an Ultrasonic Pressure Field", *Ultrasound in Med, & Biol. 31* 2005, 857-864.

Hager, F. et al., "A Summary of All Forces Acting on Spherical Particles in a Sound Field", *Proc. Of the Ultrasonic International '91 Conference and Exhibition, Le Touquet, France* 1991, 1-4.

Hamilton, Mark F. et al., "Acoustic streaming generated by standing waves in two-dimensional channels of arbitrary width", *J. Acoust. Soc. Am. 113* 2003, 153-160.

Hamilton, Mark F. et al., "Linear and nonlinear frequency shifts in acoustical resonators with varying cross sections", *J. Acoust. Soc. Am. 110* 2001, 109-119.

Harris, N. R. et al., "A silicon microfluidic ultrasonic separator", *Sensors and Actuators 95* 2003, 425-434.

Hatanaka, Shin-Ichi et al., "Effect of Process Parameters on Ultrasonic Separation of Dispersed Particles in Liquid", *Jpn. J. Appl. Phys. 38* 1999, 3096-3100.

Hawkes, Jeremy J. et al., "Force field particle filter, combinin ultrasound standing waves and laminar flow", *Sensors and Actuators B 75* 2001, 213-222.

Hawkes, Jeremy J. et al., "Microparticle manipulation in millimetre scale ultrasonic standind wave chambers", *Ultrasonics 36* 1998, 925-931.

Hawkes, Jeremy J. et al., "Single half-wavelength ultrasonic particle filter: Predictions of the transfer matrix multilayer resonator model and experimental filtration results", *J. Acoust. Soc. Am. 111* 2002, 1259-1266.

Hertz, H. M. et al., "Standing-wave acoustic trap for nonintrusive positioning of microparticles", *J. Appl. Phys. 78* 1995, 4845-4849.

Hill, Martyn et al., "Modelling in the design of a flow-through ultrasonic separator", *Ultrasonics 38* 2000, 662-665.

Hill, Martyn et al., "Modelling of layered resonators for ultrasonic separation", *Ultrasonics 40* 2002, 385-392.

Hill, Daniel H. et al., "Operating Characteristics of Acoustically Driven Filtration Processes for Particulate Suspensions", *Sep. Sci. and Tech. 35* 2000, 1363-1375.

Hill, Martyn et al., "The selection of layer thicknesses to control acoustic radiation forces profiles in layered resonators", *J. Acoust. Soc. Am. 114* (5) 2003, 2654-24661.

Holwill, Ian L. et al., "The use of ultrasonic standing waves to enhance optical particle sizing equipment", *Ultrasonics 38* 2000, 650-653.

Kaduchak, Gregory et al., "E6 diffraction catastrophe of the primary rainbow of oblate water drops: observations with white-light and laser illumination", *Applied Optics 33* 1994, 4691-4696.

Kaduchak, Gregory et al., "Hyperbolic umbilic and E6 diffraction catastrophes associated with the secondary rainbow of oblate water drops: observations with laser illumination", *Applied Optics 33* 1994, 4697-4701.

Kapishnikov, Sergey et al., "Continuous particle size separation and size sorting using ultrasound in a microchannel", *J. Stat. Mech.* 2006, 1-13.

Karumanchi, R. S. et al., "Field-assisted extraction of cells, particles and macromolecules", *Trends in Biotechnology* vol. 20, No. 2 Feb. 2002, 72-78.

Karumanchi, Raghavarao S. et al., "Field-assisted extraction of cells, particles and macromolecules", *TRENDS is Biotech 20* 2002, 72-78.

Kilburn, D. G. et al., "Enhanced Sedimentation of Mammalian Cells following Acoustic Aggregation", *Biotech. And Bioeng. 34* 1989, 559-562.

Kozuka, Teruyuki et al., "Acoustic Micromanipulation Using a Multi-Electrode Transducer", *7th Inter. Symp. On Micro Machine and Human Science* IEEE 1996, 163-170.

Kozuka, Teruyuki et al., "Control of a Standing Wave Field Using a Line-Focused Transducer for Two-Dimensional Manipulation of Particles", *Jpn. J. Appl. Phys. 37* 1998, 2974-2978.

Kozuka, Teruyuki et al., "Micromanipulation Using a Focused Ultrasonic Standing Wave Field", *Electronics and Communications in Japan 83* 2000, 1654-1659.

Kuznetsova, Larisa A. et al., "Cavitation buble-driven cell and particle behavior in a ultrasound standing wave", *J. Acoust. Soc. Am. 117* 2005, 104-112.

Kuznetsova, Larisa A. et al., "Microparticle concentration in short path length ultrasonic resonators: Roles of radiation pressure and acoustic streaming", *J. Acoust. Soc. Am. 116* 2004, 1956-1966.

Kwiatkowski, Christopher S. et al., "Resonator frequency shift due to ultrasonically induced microparticle migration in an aqueous suspension: Observations and model for the maximum frequency shift", *J. Acoust. Soc. Am. 103* 1998, 3290-3300.

Lilliehorn, Tobias et al., "Trapping of microparticles in the rear field of an ultrasonic transducer", *Ultrasonics 43* 2005, 293-303.

Lofstedt, Ritva et al., "Theory of long wavelength acoustic radiation pressure", *J. Acoust. Soc. Am. 90* 1991, 2027-2033.

Mandralis, Z. et al., "Enhanced synchronized ultrasonic and flow-field fractionation of suspensions", *Ultrasonics 32* 1994, 113-121.

Mandralis, Z. I. et al., "Transient Response of Fine Particle Suspensions to Mild Planar Ultrasonic Fields", *Fluid/Particle Separation Journal* 1990, 115-121.

Marston, Philip L. et al., "Generalized rainbows and unfolded glories of oblate drops: organization for multiple internal reflection and extension of cusps into Alexander's dark band", *Applied Optics 33* 1994, 4702-4713.

Marston, Philip L. et al., "Manipulation of Fluid Objects with Acoustic Radiation Pressure", *Ann. N.Y. Acad. Sci. 1027* 2004, 414-434.

Marston, P. L. et al., "Resonances, Radiation Pressure, and Optical Scattering Phenomena of Drops and Bubbles", *Proceedings of the Second International Colloquium on Drops and Bubbles, Jet Prop. Lab. Pub 82-7* Pasadena, CA. 1982, 166-174.

Mazumdar, M. K. et al., "Span Analyzer: Its Application to Aerodynamic Size Distribution Measurement", *J. Aerosol Sci. 10* 1979, 561-569.

Mazumder, M. K. et al., "Single particle aerodynamic relaxation time analyzer", *Rev. Sci. Instrum. 48* 1977, 622-624.

Morgan, J. et al., "Manipulation of in vitro toxicant sensors in an ultrasonic standing wave", *Toxicology in Vitro 18* 2004, 115-120.

Neild, A. et al., "Design, modeling and characterization of microfluidic devices for ultrasonic manipulation", *Sensors and Actuators B: Chemical* vol. 121, Issue 2 Feb. 20, 2007.

Nilsson, Andreas et al., "Acoustic control of suspended particles in micro fluidic chips", *Lab Chip 4* 2004, 131-135.

Nowotny, Helmut et al., "Layered piezoelectric resonators with an arbitrary number electrodes (general one-dimensional treatment)", *J. Acoust. Soc. Am. 90* 1991, 1238-1245.

Pangu, Gautam D. et al., "Acoustically aided separation of oil droplets from aqueous emulsions", *Chem. Eng. Sci. 59* 2004, 3183-3193.

Petersson, Filip et al., "Continuous separation of lipid particles from erythrocytes by means of laminar flow and acoustic standing wave forces", Lab Chip 5 2005, 20-22.

Pui, Phylis W. et al., "Batch and Semicontinuous Aggregattion and Sedimentation of Hybridoma Cells by Acoustic Resonance Fields", *Biotechnol. Prog. 11* 1995, 146-152.

Rudnick, Joseph et al., "Oscillational instabilities in single-mode acoustic levitators", *J. Acoust. Soc. Am. 87* 1990, 81-92.

Saito, Mitsunori et al., "Microorganism manipulation and microparticle arrangement by the use of ultrasonic standing waves", *SPIE 4590* 2001, 26-37.

Saito, Mitsunori et al., "Ultrasonic manipulation of locomotive microorganisms and evaluation of their activity", *J. App. Physics 92* 2002, 7581-7586.

Saito, Mitsunori et al., "Ultrasonic trapping of paramecia and estimation of their locomotive force", *Appl. Phys. Lett 71* 1997, 1909-1911.

Saito, Mitsunori et al., "Ultrasonic waves for fabricating lattice structure in composite materials", *SPIE 3786* 1999, 179-190.

Sato, Masanori et al., "Quantum mechanical representation of acoustic streaming and acoustic radiation pressure", *Physical Review E 64* 2001, 026311-1-026311-5.

Schmid, M. et al., "A computer-controlled system for the measurement of complete admittance spectra of piezoelectric resonators", *Meas. Sci. Technol. 1* 1990, 970-975.

Simpson, Harry J. et al., "Ultrasonic four-wave mixing mediated by an aqueous suspension of microspheres: Theoretical steady-state properties", *J. Acoust. Soc. Am. 98* 1995, 1731-1741.

Skudrzyk, E. et al., "Die Grundlagen der Akustic", *Springer Verlag, Wien* 1954, 202-205 and 807-825.

Sobanski, Michael A. et al., "Sub-micron particle manipulation in an ultrasonic standing wave: Applications in detection of clinically important biomolecules", *Bioseparation 9* 2001, 351-357.

Takeuchi, Masao et al., "Ultrasonic Micromanipulation of Small Particles in Liquid", *Jpn. J. Appl. Phys. 33* 1994, 3045-3047.

Takeuchi, Masao et al., "Ultrasonic Micromanipulator Using Visual Feedback", *Jpn. J. Appl. Phys. 35* 1996, 3244-3247.

Tolt, Thomas L. et al., "Separation devices based on forced coincidence response of fluid-filled pipes", *J. Acoust. Soc. Am. 91* 1992, 3152-3156.

Tolt, Thomas L. et al., "Separation of Dispersed Phases from Liquids in Acoustically Driven Chambers", *Chem. Eng. Science 48* 1993, 527-540.

Townsend, R. J. et al., "Modelling of particle paths passing through an ultrasonic standing wave", *Ultrasonics 42* 2004, 319-324.

Trihn, E. H. et al., "Experimental study of streaming flows associated with ultrasonic levitators", *Phys. Fluids 6* 1994, 3567-3579.

Tuckermann, Rudolf et al., "Trapping of heavy gases in stationary ultrasonic fields", *Chem. Phys. Ltrs. 363* 2002, 349-354.

Vainshtein, P. et al., "On the Drift of Aerosol Particles in Sonic Fields", *J. Aerosol Sci. 23* 1992, 631-637.

Vainshtein, P. et al., "The effect of centreline particle concentration in a wave tube", *J. Fluid Mech. 306* 1996, 31-42.

Verpoorte, Elisabeth et al., "Beads and chips: new recipes for analysis—Elisabeth Verpoorte reviews particle handling in microchannels", *Lab Chip 3* 2003, 60N-68N.

Visuri, S. V. et al., "Microfluidic tolls for biological sample preparation", *Poster 1423, 2nd Annual International IEEE-EMBS Special Topic Cofnerence on Microtechnologies in Medicine & Biology*, May 2-24, 2002, 556-559.

Weiser, M. A. et al., "Interparticle Forces on Red Cells in a Standing Wave Field", *Acustica 56* 1984, 114-119.

Yasuda, Kenji et al., "Concentration and Fractionation of Small Particles in Liquid by Ultrasound", *Jpn. J. Appl. Phys. 34* 1995, 2715-2720.

Yasuda, Kenji et al., "Deoxyribonucleic acid concentration using acoustic radiation force", *J. Acoust. Soc. Am. 99* 1996, 1248-1251.

Yasuda, Kenji et al., "Non-destructive, non-contact handling method for biomaterials in micro-chamber by ultrasound", *Sensors and Actuators 64* 2000, 128-135.

Yasuda, Kenji et al., "Particle separation using acoustic radiation force and elecrostatic force", *J. Acoust. Soc. Am. 99* 1996, 1965-1970.

Yosioka, K. et al., "Acoustic Radiation Pressure on a Comressible Sphere", *Acustica 5* 1955, 167-173.

Borisov, Sergey M. et al., "Blue LED Excitable Temperature Sensors Based on a New Eurpium (III) Chelate", *J. Fluoresc 18* 2008, 581-589.

Hancock, Andrew, "Observation of Forces on Microparticles in Acoustic Standing Waves", *Thesis, submitted in partial satisfaction of the requirements for the degree of Master of Science in Biomedical Engineering, University of California, Davis* 2001, 1-155.

Invitrogen, "Fluo-4 NW Calcium Assay Kits (F36205, F36206)", *Product Information* 2006.

Invitrogen, "Fluorophore selection guide for flow cytometry", *Cellular Analysis* 2007.

Lakowicz, Joseph R. et al., "On the Possibility of Long-Wavelength Long-Lifetime High-Quantum-Yield Luminophores", *Analytical Biochemistry 288* 2001, 62-75.

Mccartin, Brian J., "A Numerical Procedure for 2D Acoustic Waveguides with Heated Walls", http://flux.aps.org/meetings/YR99/OSS99/abs/S700004.html 1999.

Petersson, Filip, "Particle Flow Switch Utilizing Ultrasonic Particle Switching in Microfluidic Channels", *7th International Conf on Miniaturizing Chem and Biochem Analysis Systems* 2003, 879-882.

Steinkamp, John A., "A Differential Amplifier Circuit for Reducing Noise in Axial Light Loss Measurements", *Cytometry 4* 1983, 83-87.

Steinkamp, John A. et al., "Dual-Laser, Differential Fluorescence Correction Method for Reducing Cellular Background Autofluorescence", *Cytometry 7* 1986, 566-574.

Stewart, Carleton C. et al., "Resolving Leukocytes Using Axial Light Loss", *Cytometry 10* 1989, 426-432.

Tyson, Daniel S. et al., "Ruthenium (II) complex with a notably long excited state lifetime", The Royal Society of Chemistry 2000, 2355-2356.

Yuan, Jingli et al., "Lanthanide-based luminescence probes and time-resolved luminescence bioassays", *Trends in Analytical Chemistry 25* 2006, 490-500.

Neild, A., "A micro-particle positioning technique combining an ultrasound manipulator and a microgripper," J. Micromechanical Microengineering, 2006, 16, 1562-1570.

United States Patent and Trademark Office: Restriction Requirement dated Nov. 30, 2009, U.S. Appl. No. 11/982,042.

United States Patent and Trademark Office: Non-Final Office Action dated Oct. 16, 2008, U.S. Appl. No. 11/593,312.

United States Patent and Trademark Office: Final Office Action dated May 13, 2009, U.S. Appl. No. 11/593,312.

United States Patent and Trademark Office: Non-Final Office Action dated Oct. 23, 2009, U.S. Appl. No. 11/593,312.

United States Patent and Trademark Office: Non-Final Office Action dated Apr. 5, 2010, U.S. Appl. No. 11/593,312.

United States Patent and Trademark Office: Restriction Requirement dated Jul. 1, 2009, U.S. Appl. No. 11/784,928.

United States Patent and Trademark Office: Non-Final Office Action dated Dec. 30, 2009, U.S. Appl. No. 11/784,928.

Bardsley, et al., "Electroacoustic Productions of Murine Hybridomas," Journal of Immunological Methods, 129(1), Jan. 2, 1990, pp. 41-47.

Brodeur, "Acoustic Separation in a Laminar Flow," Ultrasonics Symposium, (no month available) 1994, pp. 1359-1362.

EPO Application No. EP 08733084.1: Extended European Search Report dated Mar. 24, 2010.

Hawkes, et al., "Continuous Cell Washing and Mixing Driven by an Unitrsound Standing Wave Within a Microfluidic Channel," Lab Chip, 4, Sep. 27, 2004, pp. 446-452.

International Application No. PCT/US05/26524: International Search Report dated Oct. 3, 2006.

International Application No. PCT/US08/87579: International Search Report dated Feb. 9, 2009.

International Application No. PCT/US2008/059181: International Search Report dated Jul. 25, 2008.

International Application No. PCT/US2009/031154: International Search Report dated Jul. 8, 2009.

Marston, P.L., "Tensile Strength and Visible Ultrasonic Cavitation of Superfluid 4He*," Journal of Low Temperature Physics, 25(3/4), Mar. 25, 1976, pp. 383-407.

United States Patent and Trademark Office: Notice of Allowance dated Jul 7, 2010, U.S. Appl. No. 11/593,312.

United States Patent and Trademark Office: Final Rejection dated Jul. 7, 2010, U.S. Appl. No. 11/784,928.

United States Patent and Trademark Office: Non-Final Office Action dated Jun. 10, 2010, U.S. Appl. No. 11/982,042.

Yagi, et al., "Flow Cytometry to Evaluate Theileria Sergenti Parasitemia Using the Florescent Nucleic Acid Stain SYTO16," Cytometry, 41, Jul. 17, 2000, pp. 223-225.

* cited by examiner

US 7,837,040 B2

ACOUSTIC CONCENTRATION OF PARTICLES IN FLUID FLOW

STATEMENT REGARDING FEDERALLY SPONSORED RESEARCH OR DEVELOPMENT

This invention was made with Government support under Contract Number DE-AC51-06NA25396 awarded by the United States Department of Energy. The Government has certain rights in the invention.

BACKGROUND OF THE INVENTION

The present invention relates in general to field-based separation of particles in a medium utilizing acoustic pressure.

Field-based separation of particles in fluid has been explored for numerous applications from high gradient magnetic separation of nuclear fuel waste particles to dielectrophoretic separation of live and dead bacteria to acoustic separation of blood cells from serum.

The ability to push cells or particles to the top of a channel enables concentration of particulate matter in fluids by forcing them to slower streamlines in a laminar flow regime or by trapping them altogether if the viscous drag is less than the trapping force. Particles and/or cells so trapped can also be held and washed or exposed to other fluids and/or reagents.

It is desirable to provide a device for acoustic concentration and trapping of particles within a medium using acoustic radiation pressure.

BRIEF SUMMARY OF THE INVENTION

An apparatus and method for acoustic concentration of particles in a fluid flow includes a substantially acoustically transparent membrane and a vibration generator that define a fluid flow path therebetween. The fluid flow path is in fluid communication with a fluid source and a fluid outlet and the vibration generator is disposed adjacent the fluid flow path and is capable of producing an acoustic field in the fluid flow path. The acoustic field produces at least one pressure minima in the fluid flow path at a predetermined location within the fluid flow path and forces predetermined particles in the fluid flow path to the at least one pressure minima.

In one embodiment, the membrane may be formed from biaxially-oriented polyethylene terephthalate (boPET) polyester film (Mylar®), glass mica, polymers, or combinations thereof. The predetermined location in the fluid flow path may be adjacent a membrane wall. The predetermined dimension may be a function of the resonance of the fluid source. The predetermined location may be a function of a wavelength of the acoustic field produced by the vibration generator and may be ¼ of the wavelength of the acoustic field or ¾ of the wavelength of the acoustic field. The vibration generator may be a piezoelectric transducer. The predetermined particles may be positive acoustic contrast particles.

Alternatively, the membrane is permeable. Reagents may diffuse through the membrane to the predetermined particles in the flow path when flow is stopped in the flow path. Alternatively, the apparatus further comprises a matching layer intermediate the vibration generator and the flow path. The matching layer may be a ¼ wavelength matching layer. Alternatively, the wall of the membrane accommodates high power microscopic observation of the particles in the flow path. The predetermined particles may be particles selected from the group consisting of particles of different sizes and particles with different acoustic contrasts and the apparatus may perform field flow fractionation.

The present invention comprises an apparatus and method used to separate, concentrate, trap or focus particles in fluid using ultrasonic standing waves. The apparatuses are preferably constructed using a vibration generator such as a piezoelectric transducer to drive resonant modes in a channel or chamber with a membrane top such that particles with positive acoustic contrast are driven to the membrane or to other points of minimum pressure in the standing wave generated by the vibration generator.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Successful meso- to microfluidic sample preparation is dependent upon efficient sorting, concentration, and washing of targets. Numerous successful analytical lab-on-a-chip micro-devices capable of a wide range of detection techniques from spectroscopy to gene detection have been demonstrated in both clinical and homeland security arenas. In the present evolution of these devices, however, their increased application to real world problems of interest has been severely limited by inadequate provisions for handling samples. The heart of this problem lies in concentrating and purifying a large dilute sample that contains interferents. These microfabricated devices generally require a clean sample with a representative population of target species that can be analyzed only in microliter and nanoliter volumes. In applications where the sample volume is measured in milliliters to liters, the sample preparation is a daunting task that has not been adequately addressed.

Several field-based methods for sample processing have been applied to this problem including immunomagnetic separation, electrophoresis, dielectrophoresis and ultrasonic separation. Ultrasonic separation is particularly attractive for many applications as it typically does not require reagents and can be performed in complex media with little regard for sample conductivity or pH.

Ultrasonic separation is typically achieved in resonant chambers in which standing waves are established using a vibration generator, such as a piezoelectric transducer or the like. The force on a particle is given by the following equation derived by Gor'kov:

$$F = -\nabla\left(\frac{2}{3}\pi R^3 \left[\frac{Z_0}{\rho_f c_f^2}\overline{p^2} - \frac{3Z_1\rho_f}{2}\overline{v^2}\right]\right)$$

Where R is particle radius, $\rho_f$ is fluid density $c_f$ is fluid sound speed $p^2$ is mean square fluctuations of pressure at the particle, $v^2$ is mean square fluctuations of velocity at the particle and $Z_0$ and $Z_1$ are functions of particle and fluid properties called acoustic contrast factors. Most particles and cells of interest have positive acoustic contrast in water or buffers and therefore they typically migrate to positions of lowest pressure (pressure nodes or pressure minima). Materials such as fat globules and gas bubbles have negative acoustic contrast and tend to move toward positions of highest pressure (pressure antinodes or pressure maxima).

Figure 1:
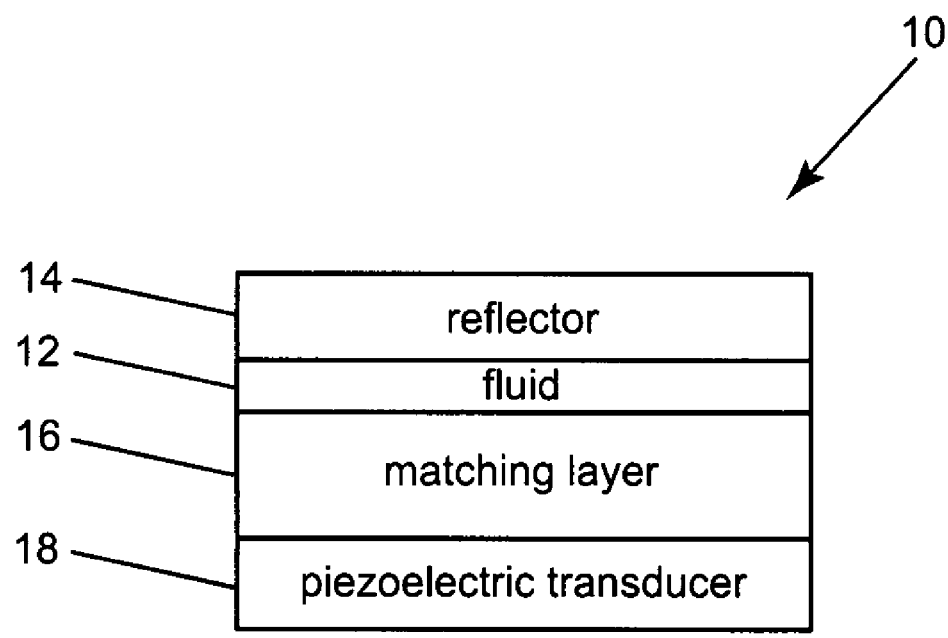
FIG. 1 is a schematic view of a separator according to the prior art.

Referring to FIG. 1, an ultrasonic separator in accordance with the prior art is indicated generally at 10. Separator 10 includes fluid channel 12, ½ wavelength glass acoustic reflector top 14 and ¾ wavelength matching layer resonator bottom 16 coupled to transducer 18. Typically, separator 10 operates at a resonant frequency approximately ½ or ¼ wavelength of fluid layer 12. The thickness and composition of the material of top reflector 14 and bottom matching layer 16 are chosen such that the phase relationship of incident and reflected waves results in a pressure node or pressure minima either at the center of fluid channel 12 or at the surface of the top reflector 14. Separator 10 uses acoustic standing waves in channel 12 to force particles with positive acoustic contrast to move towards one wall of the channel. Device 10 is tuned such that a standing wave can be established for which a pressure node or minima forces particles with positive acoustic contrast to migrate toward top of channel 12.

Figure 2:
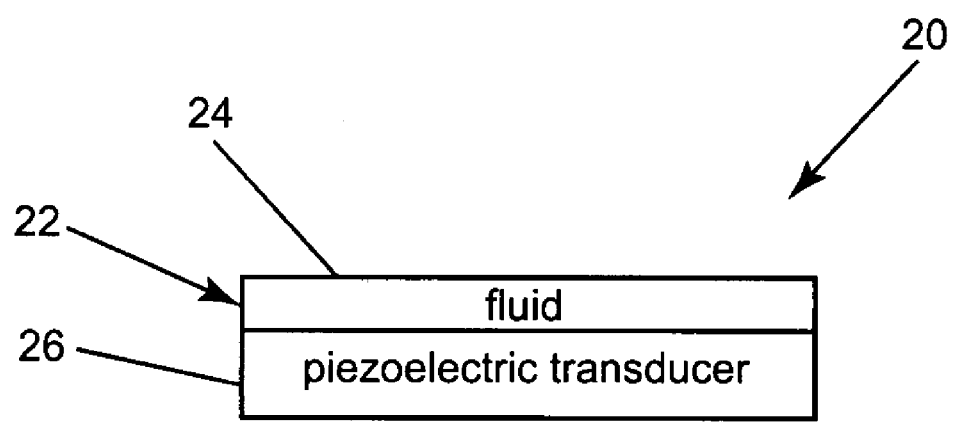
FIG. 2 is a schematic view of an embodiment of an apparatus in accordance with the present invention.

Referring to FIG. 2, an embodiment of apparatus in accordance with the present invention is indicated generally at 20. Apparatus 20 includes fluid flow path or channel 22 preferably in fluid communication with a fluid source (not shown) and a fluid outlet (not shown) having membrane 24 as a top surface coupled to vibration generator 26 disposed adjacent flow channel 22. Flow channel 22 is preferably. defined by an upper surface of vibration generator 26 and by membrane 24. The fluid source may supply water, or any suitable liquid to flow path or channel 22, as will be appreciated by those skilled in the art. Fluid flow path or channel 22 preferably has a predetermined dimension that is a function of the resonance of the fluid source. Preferably, vibration generator 26 is a piezoelectric transducer. Alternatively, vibration generator 26 is a line-drive element, a displacement generator, or any other type of vibration generator capable of producing an acoustic or displacement field within fluid channel 22. When vibration generator 26 is driven, plane waves incident on the boundary of membrane 24 are reflected back out of phase. Membrane 24 functions as a pressure release surface with a reflection coefficient of near −1. Therefore, the reflected wave is 180 degrees out of phase with the incident wave and the pressure wave is 90 degrees out of phase with the displacement wave. This results in a pressure node or minima at the surface of membrane 24, best seen in FIG. 3 and discussed in more detail below. Membrane 24 can be made of any suitable material but it should be thin enough to be substantially acoustically transparent to the acoustic wave generated by vibration generator 26 such as, but not limited to, thin Mylar®, glass, mica or similar suitable materials.

Figure 3:
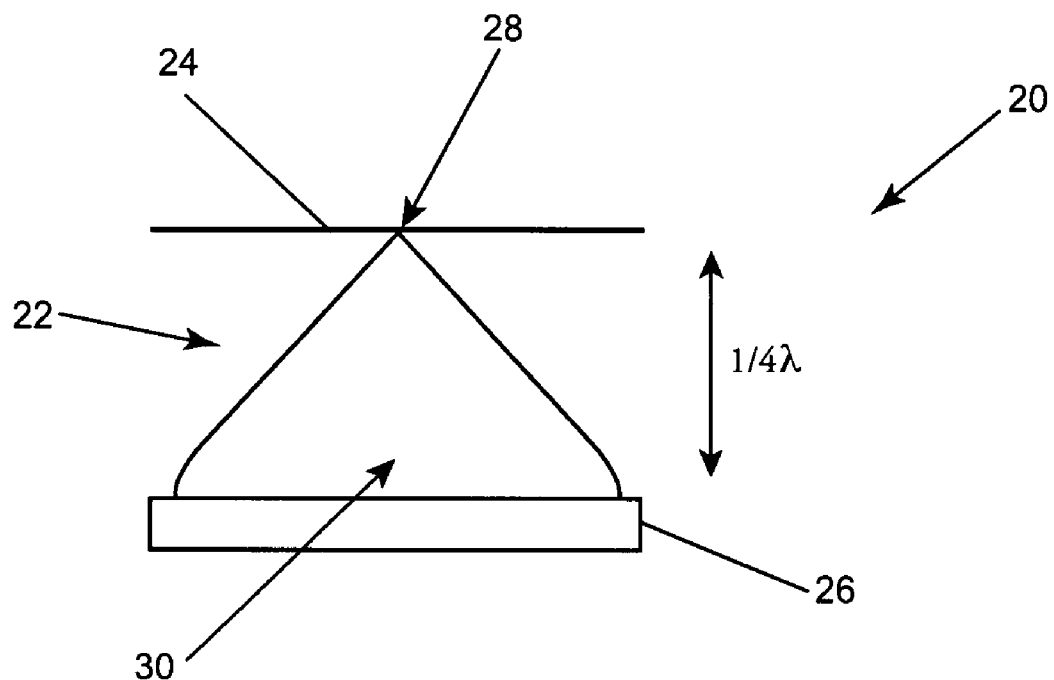
FIG. 3 is a schematic graph showing the location of pressure nodes and antinodes in the apparatus of FIG. 2.
Figure 6:
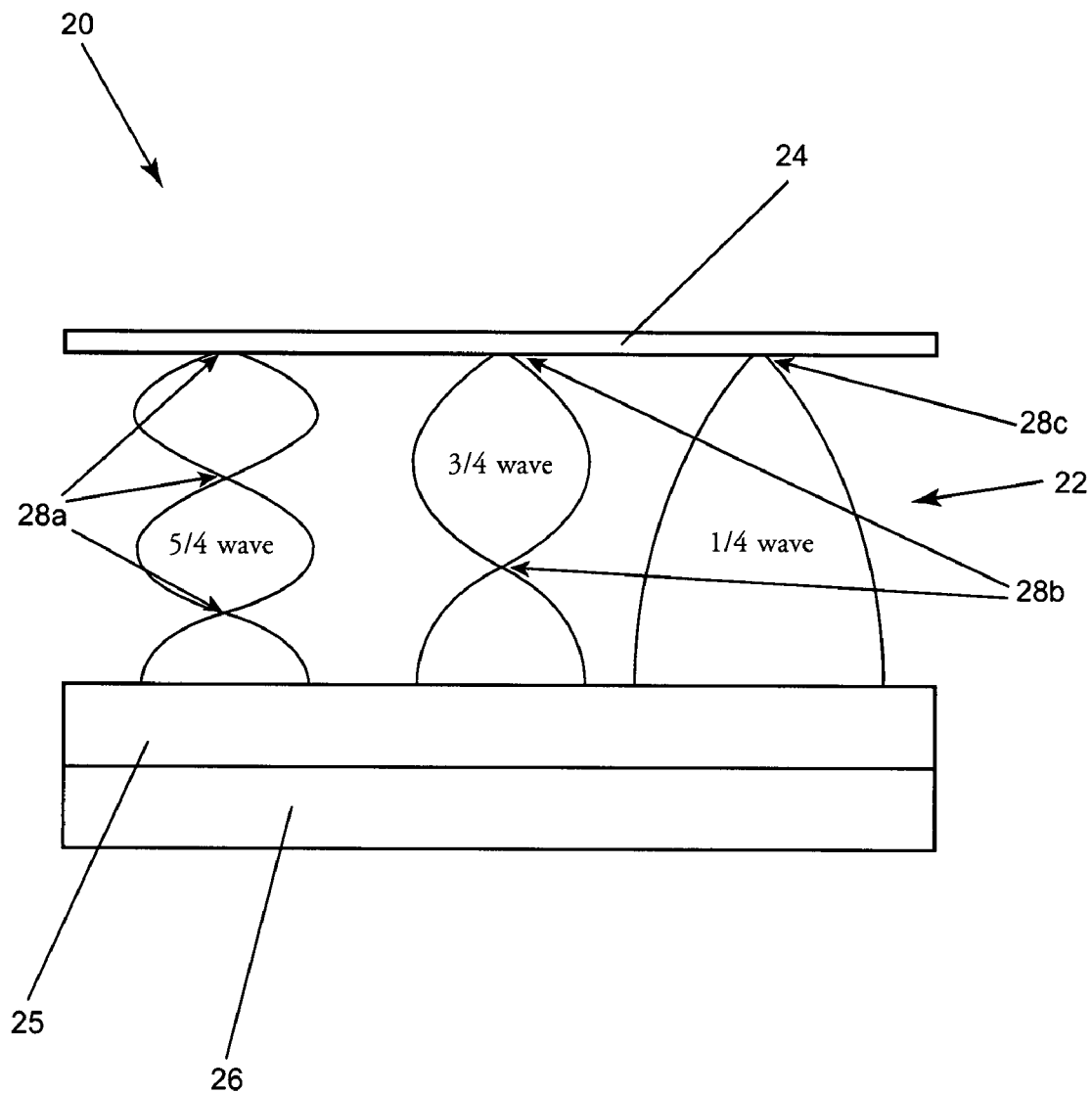
FIG. 6 is a schematic view of an embodiment of an apparatus in accordance with the present invention showing profiles of various pressure minima.

There is shown in FIG. 3 a pressure profile in fluid flow path or channel 22 indicating pressure node or minima 28 adjacent membrane 24 and pressure antinode or maxima 30 adjacent vibration generator 26. The thickness of channel 22 thickness is ¼ wavelength (λ) of the resonance. Particles and/or cells with positive acoustic contrast are driven to the surface of membrane 24 surface or pressure node 28. Pressure nodes 28 can also be created within the fluid by tuning fluid layer 22 to alternate frequencies e.g. ¾ or ⅝ λ. For example, there is shown in FIG. 6, various locations of pressure minima 28a, 28b, and 28c in flow path or channel 22 of apparatus 20, based on the resonance of medium disposed in the fluid layer in flow channel 22. Pressure minima 28a for a ⅝ wavelength is shown in three locations within channel 22. Pressure minima 28b for a ¾ wavelength is shown at a pair of locations within channel 22 and pressure minima 28c for a ¼ wavelength is shown at a single location adjacent membrane 24. Those skilled in the art will appreciate that pressure minima, such as pressure minima 28a, 28b, and 28c may be located at any predetermined location within channel 22 between vibration generator 26 and membrane 24 and that the predetermined location is a function of the resonance and frequency of the fluid source and the predetermined dimension of flow channel 22 between vibration generator 26 and membrane 24. Alternatively, apparatus 20 includes a ¼ wavelength matching layer 25 on an upper surface of vibration generator 26 opposite membrane 24. Matching layer 25 is preferably a ¼ wavelength matching layer and is operable to isolate vibration generator 26 from the fluid within channel 22 and/or to better match the acoustic impedance of the fluid within channel 22.

Figure 4:
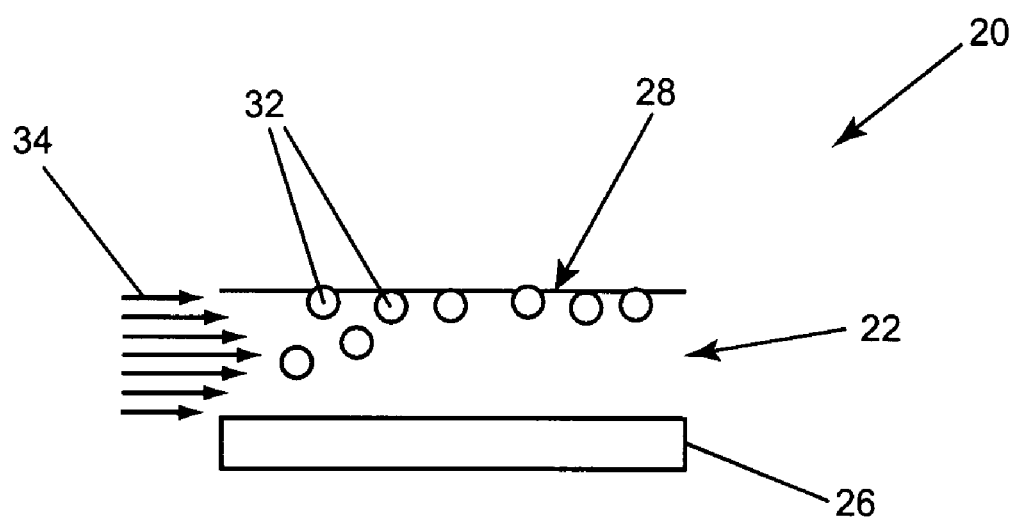
FIG. 4 is a schematic view of particles being separated by the apparatus of FIG. 2.

Apparatus 20 can be applied to separate and or concentrate target particles and cells. When device 20 is embodied as a channel 22 with laminar flow, indicated by arrow 34, particles or cells 32 are forced into slower streamlines where they become concentrated, best seen in FIG. 4. For particles 32 of different sizes or with different acoustic contrasts, device 20 can perform field flow fractionation (FFF), as will be appreciated by those skilled in the art. In FIG. 4, particles or cells 32 with larger volumes or greater acoustic contrast are forced to surface of membrane 24 more quickly.

Alternatively, when the flow of the fluid in device 20 is slowed sufficiently or stopped altogether, particles or cells 32 are trapped at surface of membrane 24. There, particles or cells 32 are washed or exposed to other reagents. This is preferably done by replacing the sample fluid in channel 22 or, if membrane 24 is made permeable, reagents are preferably added to the opposite side of membrane 24 where the reagents can diffuse through membrane 24 to the trapped targets 32.

Figure 5A:
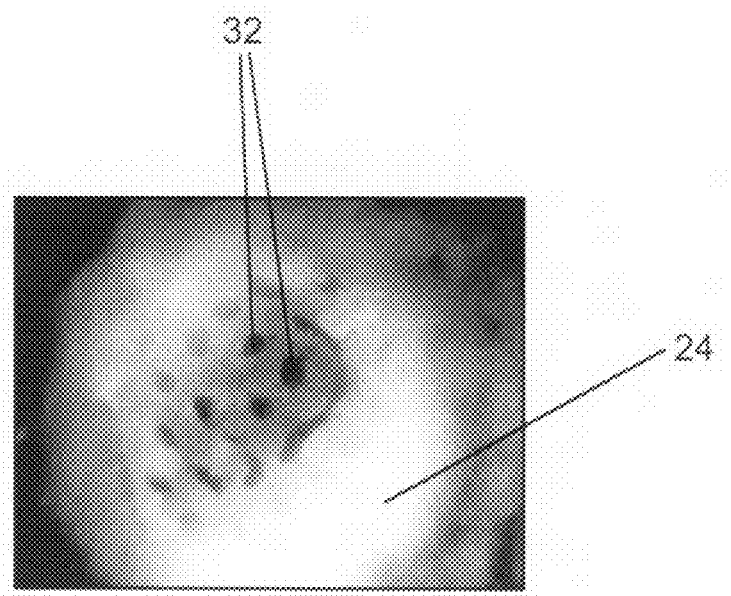
FIGS. 5a and 5b are microscopic photographs showing latex particles acoustically trapped on a membrane surface of the apparatus.
Figure 5B:
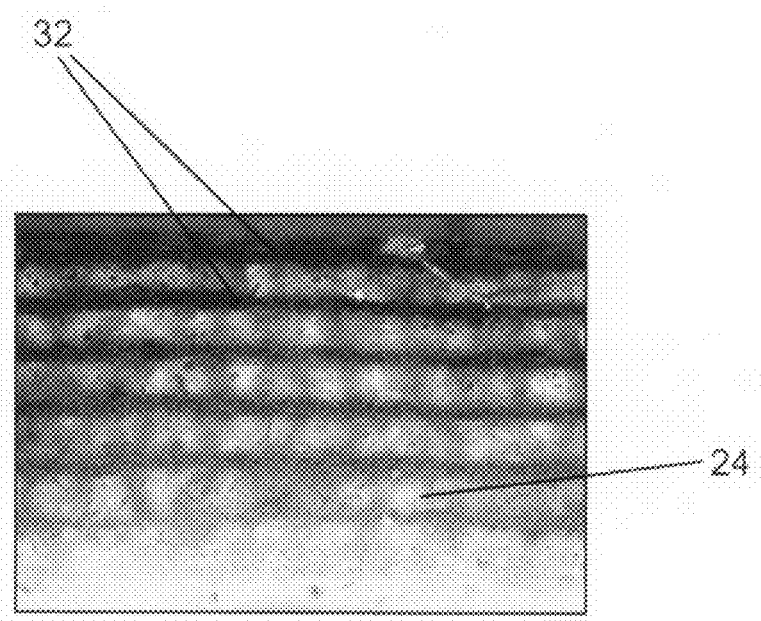

Thin membrane 24 advantageously allows optical observation with high numerical aperture close working distance lenses (not shown). This is useful in applications in oncology or microbiology. In addition, cells or particles 32 can be observed in an imaging plane in flow away from the membrane if an alternate tuning that provides for pressure nodes or minima in the fluid is used. In FIGS. 5a and 5b there is shown microscopic photographs of test results for apparatus 20 using 3 micron red latex particles 32. Particles 32 are trapped on the surface of membrane 24.

For apparatus 20, it is only necessary to tune to the resonance of the fluid layer (¼, ¾, ⅝, etc wavelength). It is therefore simpler to accommodate fluid property or temperature changes that may affect the tuning of apparatus 20. Added advantages to the membrane configuration of apparatus 20 include possible viewing of trapped or moving plane focused species with close working distance objectives and possible incorporation of particular membrane properties, such as selective permeability.

Acoustic separations utilizing apparatus 20 can advantageously be accomplished without the use of reagents and without regard for fluid pH or conductivity, making apparatus 20 well suited for use in complex media such as blood or sewer water. Apparatus 20 uses membrane top 24 that can be fabricated inexpensively from polymers. Membrane top 24 is thin enough to accommodate high power microscopic observation of trapped species 32. Membrane 24 can also advantageously be made selectively permeable such that reagents or analytes could diffuse across membrane 24.

The primary commercial applications for apparatus 20 are contemplated to be sample preparation (concentration/separation/washing) and imaging for medical, industrial, and environmental samples. Apparatus 20 of the present invention pushes positive acoustic contrast particles 32 to channel wall 24 opposite vibration generator 26 that comprises a thin membrane top 24, which advantageously eliminates the need for precise tuning of paired matching layer 16 and reflector 14 as in the prior art device 10 shown in FIG. 1.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above and/or in the attachments, and of the corresponding application(s), are hereby incorporated by reference.

What is claimed is:

1. An apparatus for acoustic concentration of particles in a fluid flow, comprising:
    a flow channel;
    a substantially acoustically transparent membrane disposed at a top surface of said flow channel;
    a vibration generator, said vibration generator and said membrane defining a fluid flow path therebetween, said fluid flow path in fluid communication with a fluid source and a fluid outlet and having a predetermined dimension, said vibration generator disposed adjacent said fluid flow path and operable to produce an acoustic field in said fluid flow path, said acoustic field producing at least one pressure minima in said fluid flow path at a predetermined location within said fluid flow path, and wherein the membrane is configured to reflect an acoustic wave generated by the vibration generator back into said fluid flow path, such that the reflected acoustic wave is out of phase with the acoustic wave generated by the vibration generator.

2. The apparatus of claim 1 wherein said membrane is formed from at least one material selected from the group consisting of Mylar®, glass mica, polymers, and any combination thereof.

3. The apparatus of claim 1 wherein said predetermined location in said fluid flow path is adjacent a membrane wall.

4. The apparatus of claim 1 wherein said predetermined dimension is a function of the resonance of the fluid source.

5. The apparatus of claim 1 wherein said predetermined location is a function of a wavelength of said acoustic field produced by said vibration generator.

6. The apparatus of claim 4 wherein said predetermined location is ¼ of said wavelength of said acoustic field.

7. The apparatus of claim 4 wherein said predetermined location is ⅝ of said wavelength of said acoustic field.

8. The apparatus of claim 1 wherein said vibration generator is a piezoelectric transducer.

9. The apparatus of claim 1 wherein said predetermined particles are positive acoustic contrast particles.

10. The apparatus of claim 1 wherein said membrane is permeable.

11. The apparatus of claim 9 wherein reagents diffuse through said membrane to said predetermined particles in said flow path when flow is stopped in said flow path.

12. The apparatus of claim 1 further comprising a matching layer intermediate said vibration generator and said flow path.

13. The apparatus of claim 12 wherein said matching layer is a ¼ wavelength matching layer.

14. The apparatus of claim 1 wherein a wall of said membrane accommodates high power microscopic observation of said particles in said flow path.

15. The apparatus of claim 1 wherein said predetermined particles are particles selected from the group consisting of particles of different sizes and particles with different acoustic contrasts and wherein said apparatus performs field flow fractionation.

16. A method for concentrating and trapping particles in a fluid flow, comprising:
    disposing a substantially acoustically transparent membrane at a top surface of a flow channel;
    driving a vibration generator and producing an acoustic field, the acoustic field producing at least one pressure minima in the fluid flow path at a predetermined location and forcing predetermined particles in the fluid flow to the at least one pressure minima
    wherein a flow path is defined between the vibration generator and the membrane, and the membrane is configured to reflect an acoustic wave generated in the fluid flow path by the vibration generator back into said fluid flow path, and wherein the reflected acoustic wave is out of phase with the acoustic wave generated by the vibration generator.

17. The method of claim 16 wherein the membrane is formed from at least one material selected from the group consisting of Mylar®, glass mica, polymers, and a combination thereof.

18. The method of claim 16 wherein the predetermined dimension is a function of the resonance of the fluid source.

19. The method of claim 16 wherein the predetermined location is a function of a wavelength of the acoustic field produced by the vibration generator.

20. The method of claim 19 wherein the predetermined location is ¼ of the wavelength of the acoustic field.

21. The method of claim 19 wherein the predetermined location is ⅝ of the wavelength of the acoustic field.

22. The method of claim 16 wherein the vibration generator is a piezoelectric transducer.

23. The method of claim 16 wherein the predetermined particles are positive acoustic contrast particles.

24. The method of claim 16 wherein the membrane is permeable.

25. The method of claim 24 further comprising the step of diffusing reagents through the membrane to the predetermined particles in the flow path when flow is stopped in the flow path.

26. The method of claim 16 further comprising the step of providing a matching layer intermediate the vibration generator and the flow path.

27. The method of claim 26 wherein the matching layer is a ¼ wavelength matching layer.

28. The method of claim 16 further wherein a wall of the membrane accommodates high power microscopic observation of the particles in the flow path.

29. The method of claim 16 wherein the predetermined particles are particles selected from the group consisting of particles of different sizes and particles with different acoustic contrasts.

30. The method of claim 16 further comprising the step of performing field flow fractionation.

31. The method of claim 16 wherein the predetermined location is adjacent a membrane wall.

* * * * *